United States Patent
Kaulen et al.

(10) Patent No.: US 8,207,224 B2
(45) Date of Patent: Jun. 26, 2012

(54) PRESERVATIVES BASED ON CARBOXYLIC ANHYDRIDES

(75) Inventors: Johannes Kaulen, Odenthal (DE); Erasmus Vogl, Leverkusen (DE); Edwin Ritzer, Leverkusen (DE); Manfred Hoffmann, Kempen (DE)

(73) Assignee: LANXESS Deutchland GmbH, Leverkusen (DE)

( * ) Notice: Subject to any disclaimer, the term of this patent is extended or adjusted under 35 U.S.C. 154(b) by 136 days.

(21) Appl. No.: 12/373,923

(22) PCT Filed: Jul. 18, 2007

(86) PCT No.: PCT/EP2007/006361
§ 371 (c)(1),
(2), (4) Date: Jan. 15, 2009

(87) PCT Pub. No.: WO2008/014889
PCT Pub. Date: Feb. 7, 2008

(65) Prior Publication Data
US 2009/0264532 A1    Oct. 22, 2009

(30) Foreign Application Priority Data
Jul. 29, 2006  (DE) .......................... 10 2006 035 202

(51) Int. Cl.
*A61K 31/185* (2006.01)
*A01N 37/00* (2006.01)

(52) U.S. Cl. ..................................... 514/553; 426/330.3
(58) Field of Classification Search .................. None
See application file for complete search history.

(56) References Cited

U.S. PATENT DOCUMENTS

| 3,097,996 A | 7/1963 | Thoma et al. ................... 167/22 |
| 2002/0197185 A1 | 12/2002 | Jamiolkowski et al. ........ 422/29 |

FOREIGN PATENT DOCUMENTS

| DE | 1 961 922 | 6/1971 |
| FR | 2 877 576 | 5/2006 |
| WO | 2004/056214 | 7/2004 |
| WO | 2007/008874 | 1/2007 |

OTHER PUBLICATIONS

Weng et al; Food Science and Technology, 1997, 30(5), pp. 485-487; "Sorbic Anhydride as Antimycotic Additive in Polyethylene Food Packaging Films".
Divol, B. et al; Food Microbiology, Academic Press Ltd, London, GB; Bd. 22, Nr. 2-3; Apr. 1, 2005, pp. 169-178; "Effectiveness of dimethyldicarbonate to stop alcoholic fermentation in wine" XP-004613725.
Dobias Jaroslave et al: Food Additives and Contaminants, Bd. 17, Nr. 12, Dec. 2000. pp. 1047-1053; "Properties of polyethylene films with incorporated benzoic anhydride and/or Ethyl and propyl esters of 4-hydroxybenzoic acid and their suitability for food packaging" XP-009100683.

*Primary Examiner* — James D Anderson
*Assistant Examiner* — Gregg Polansky
(74) *Attorney, Agent, or Firm* — Nicanor A. Kohncke

(57) ABSTRACT

Carboxylic anhydrides are highly suitable as additive for industrial materials, cosmetics, pharmaceutics and foodstuffs, in particular beverages, for protecting them against attack and/or destruction by microorganisms.

1 Claim, No Drawings

PRESERVATIVES BASED ON CARBOXYLIC ANHYDRIDES

The invention relates to the use of carboxylic anhydrides for preserving industrial materials, cosmetics, pharmaceutics and foodstuffs.

A large number of carboxylic anhydrides and methods for their preparation have been known for a long time from the literature. A use of carboxylic anhydrides for direct preservation of industrial materials or foodstuffs has hitherto not been described. WO 2004/056214 describes a method for preparing packaging materials comprising immobilized antimicrobial substances, inter alia acid anhydrides, which are said to exert a biological action in that the active compound is transferred indirectly, namely from the packaging material, to the packaged material, thereby preserving it.

Also described are packaging films made of polyethylene which incorporate sorbic anhydride. These products are said to have a certain antifungal action (Weng, Yih-Ming; Chen, Min-Jane; Food Science and Technology, 1997, 30(5), 485-487).

Furthermore, a considerable number of processes for preserving industrial materials, cosmetics or foodstuffs in which the biocidally active compound is added directly to the product to be preserved are already known from the prior art. However, there is still a need for improvement.

Recently, in particular, biocide residues introduced by a biocide treatment into the product to be protected, for example, are more and more considered to be problematic and should be avoided, if possible.

Thus, indeed, some biocides have already been developed which "disappear" at the site of action for example by, in the most favourable case, decomposition into products which have been known for a long time, have been studied well and, in particular, are considerably less active. Examples of these which may be mentioned are compounds such as hydrogen peroxide, peroxy acids, chlorine, diethyl dicarbonate or dimethyl dicarbonate. However, there is still a large need for novel microbicidal substances which are decomposed in the medium to relatively safe substances and which, at the same time, have a better activity sectrum than the substances used hitherto. For use in cosmetics, pharmaceutics or foodstuffs, in particular, only a few of the substances available from the prior art are suitable.

Accordingly, it was an object of the present invention to provide effective biocidally active compounds which can be incorporated directly into the product to be preserved and are degraded therein to less active compounds which, in particular when used in cosmetics, pharmaceutics and foodstuffs, are considered safe.

Surprisingly, it has now been found that carboxylic anhydrides are highly suitable for the antimicrobial treatment of industrial materials, cosmetics, pharmaceutics, foodstuff and, in particular, beverages.

Accordingly, the present invention provides the use of at least one carboxylic anhydride as additive for industrial materials, cosmetics, pharmaceutics and foodstuffs for protecting them against attack and/or destruction by microorganisms.

Preferably, the carboxylic anhydrides are incorporated directly into the product to be protected.

The carboxylic anhydrides are preferably compounds of the general formula (I)

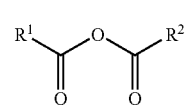

in which
$R^1$ and $R^2$ independently of one another represent straight-chain or branched $C_1$-$C_8$-alkyl, $C_3$-$C_8$-cycloalkyl, mono- or polyunsaturated $C_2$-$C_8$-alkenyl $C_5$-$C_8$-cycloalkenyl, $C_2$-$C_8$-alkynyl, phenyl, benzyl or phenethyl, each of which is optionally mono- or polysubstituted by identical or different substituents from the group consisting of methyl, hydroxyl, carboxyl, acyl, alkoxy, acyloxy and oxo,
or
$R^1$ and $R^2$ together represent a linker —$(CH_2)_n$— where n=1 to 6 or represent a linker —$CH_2$—O—$CH_2$—, —$CH_2$—$CH_2$—O—$CH_2$—, —$CH_2$—$CH_2$—O—$CH_2$—$CH_2$— or —CH=CH— where the linkers mentioned are in each case optionally mono or polysubstituted by identical or different substituents from the group consisting of methyl, hydroxyl, carboxyl, acyl, alkoxy, acyloxy and oxo.

Instead of the compounds of the formula (I), it is also possible to use oligomers or polymers of anhydrides of dicarboxylic acids derived from the bridged carboxylic anhydrides of the formula (I).

Particular preference is given to using carboxylic anhydrides of the formula (I) in which
$R^1$ and $R^2$ independently of one another represent straight-chain or branched $C_1$-$C_8$-alkyl, mono- or polyunsaturated $C_2$-$C_5$-alkenyl, phenyl or benzyl, which is in each case optionally mono- or polysubstituted by identical or different substituents from the group consisting of methyl, hydroxyl, carboxyl, acyl, alkoxy and acyloxy.

Very particular preference is given to the use of carboxylic anhydrides of the formula (I)
in which
$R^1$ and $R^2$ independently of one another represent methyl, ethyl, propyl, isopropyl, pent-1,3-dienyl, or phenyl.

Especially preferred is the use of acetic anhydride, benzoic anhydride, propionic anhydride and/or sorbic anhydride.

In the present context, industrial materials are to be understood as meaning non-living materials prepared for use in industry. The industrial materials are, for example, adhesives, sizes, paper and cardboard, textiles, leather, wood, processed wood products, wood composites, paints, cooling lubricants and other materials which can be attacked or degraded by microorganisms. In the context of the present invention, industrial materials are furthermore to be understood as meaning parts of production plants, for example cooling-water circuits, which may be impaired by the proliferation of microorganisms. Industrial materials which are preferably to be protected are adhesives, sizes, papers and cardboards, leather, wood, processed wood products, wood composites, paints, cooling lubricants and heat-transfer liquids.

The cosmetics are, for example, creams or lotions for skin-care, such as face or hand creams, or else make-up products, such as lipsticks or face masks.

The pharmaceutics are, for example, drug preparations, such as juices, drops, sprays, ointments, tablets and infusion solutions to be administered intravenously.

To protect industrial materials, cosmetics, pharmaceutics and foodstuffs, the carboxylic anhydrides are, in a suitable manner, incorporated directly into the medium to be preserved. In general, a homogeneous incorporation is advantageous and necessary. This may be achieved, for example, using suitable metering pumps. Incorporation may also be, for example, by means of agitators or mixers.

Here, the carboxylic anhydrides to be used according to the invention may be added as pure compounds or in the form of formulations to the product to be protected. In addition to the carboxylic anhydrides, such formulations also comprise one or more solvents and/or formulation auxiliaries. Suitable solvents are, depending on the solubility of the carboxylic anhydrides, water, ethanol and also suitable organic solvents.

Suitable formulation auxiliaries are, for example, surfactants, antifoams, antioxidants, stabilizers or inert organic or inorganic auxiliaries, such as, for example, cellulose fibres. The carboxylic anhydrides may also be applied to adsorptive media and used in this form. Examples of adsorptive media are cellulose fibres and activated carbon.

Here, these formulations usually comprise the carboxylic anhydrides in amounts of from 1 to 90% by weight.

Such formulations can be stored for a period of several months.

The carboxylic anhydrides to be used according to the invention are generally employed in an amount of from 1 to 100 000 ppm, preferably in an amount of from 10 to 10 000 ppm, particularly preferably in an amount of from 50 to 5000 ppm, very particularly preferably in an amount of from 100 to 2000 ppm, based on the medium to be preserved.

By the use according to the invention of the carboxylic anhydrides, it is possible to stabilize industrial materials, cosmetics, pharmaceutics and foodstuffs against biological degration reactions. Such degration reactions occur, for example, on attack by microorganisms.

Microorganisms capable of degrading or changing the industrial materials which may be mentioned are, for example, bacteria, fungi, yeasts, algae and slime organisms. The carboxylic anhydrides used according to the invention preferably act against yeasts, bacteria and fungi.

Microorganisms of the following genre may be mentioned as examples:
*Acetobacter pasteurianius*,
*Aspergillus*, such as *Aspergillus niger*,
*Candida krusei*
*Chaetomium*, such as *Chaetomium globosum*,
*Escherichia*, such as *Escherichia coli*,
*Penicillium*, such as *Penicillium glaucum*,
*Pseudomonas*, such as *Pseudomonas aeruginosa*,
*Rhodotorula*, such as *Rhodotorula rubra*
*Saccharomyces*, such as *Saccharomyces cervisiae*
*Staphylococcus*, such as *Staphylococcus aureus*.

The industrial materials, cosmetics, pharmaceutics and foodstuffss stabilized according to the invention are distinguished by a longer shelf-life.

Here, it is particularly advantageous that the carboxylic anhydrides used according to the invention can hydrolyse to give the corresponding carboxylic acids. Some of the carboxylic acids formed by gradual hydrolysis by the degradation of the carboxylic anhydrides have been known for a long time as preservatives, their toxicology has been well-studied and they contribute additionally to prolonging the preserving action. Thus the rapid temporary kill of pathogens is supplemented by a persistent preservative component.

Especially preferred is the use according to the invention of at least one carboxylic anhydride of the formula (I) for protecting beverages against attack and/or destruction by microorganisms.

Especially beverages susceptible to microbiological degradation are effectively preserved and stabilized by the carboxylic anhydrides. Thus, after appropriate sealing, the beverages preserved in this manner can be stored at room temperature for several months without any microbiological attack being observed.

Such a method of cold sterilization has a number of advantages compared, for example, to tunnel pasteurization such as energy saving or advantages with a view to apparatus required. Here, the effectiveness of the preservation according to the invention is better than existing methods of cold sterilization.

The carboxylic anhydrides to be used according to the invention are, for example, highly suitable for use as cold disinfectants for still or carbonated drinks, such as soft drinks, vitamin drinks, fruit juice drinks, tea drinks, alcoholic or dealcoholized wine drinks, fruit punches or beers. To this end, the carboxylic anhydrides are preferably added in amounts between 10 and 200 ppm close in time to packaging the beverages. Admixture to the beverages is performed using special metering pumps.

When used in beverages, the carboxylic anhydrides act so as to control a number of microorganisms, such as fermentative yeasts, moulds or fermentative bacteria. Examples which may be mentioned here are, for instance, *Saccharomyces globosum, Saccharomyces diastaticus, Saccharomyces cervisiae, Zygosaccharomyces bailii, Candida crusei, Endomyces lactis, Penicillium glaucum, Acetobacter pasteurianus, Brettanomyces* spp, *Lactobacillus brevis, Lactobacillus buchneri* and many others.

The carboxylic anhydrides to be used according to the invention can be combined in an advantageous manner with further antimicrobially active compounds.

Accordingly, the present invention furthermore provides mixtures of at least one carboxylic anhydride of the formula (I) with at least one further antimicrobially active compound, preferably from the group consisting of dimethyl dicarbonate, (diethyl dicarbonate, sorbic acid and its salts, benzoic acid and its salts, sulphur dioxide and compounds which can release sulphur dioxide, and also ortho-phenylphenol and propionic acid.

Particular preference is given to mixtures with dimethyl dicarbonate, sorbic acid and its salts or benzoic acid and its salts.

The invention also provides the use of the mixtures according to the invention for protecting industrial materials, cosmetics, pharmaceutics, foodstuffs and in particular beverages against attack and/or destruction by microorganisms.

The carboxylic anhydrides of the formula (I) and the mixtures according to the invention are also highly suitable for preserving bread. Here, the bread is, after baking, sprayed with the carboxylic anhydrides of the formula (I) or a mixture according to the invention in the form of a suitable formulation, preferably an aqueous or alcoholic solution.

The mixtures according to the invention generally comprise at least one carboxylic anhydride of the formula (I) and at least one further antimicrobially active compound in a ratio of from 1:100 to 100:1, preferably from 1:10 to 10:1 and particularly preferably 1:1.

The mixtures according to the invention are generally employed in an amount of from 1 to 100 000 ppm, preferably in an amount of from 10 to 10 000 ppm, particularly preferably in an amount of from 50 to 5000 ppm, very particularly preferably in an amount of from 100 to 2000 ppm, based on the medium to be preserved.

The mixtures according to the invention are, for example, stirred directly into the media to be preserved or added via metering pumps. Here, the mixtures according to the invention can be added directly or in the form of formulations to the product to be protected. Such formulations comprises, in addition to the components of the mixture, one or more solvents and/or formulation auxiliaries. Suitable solvents and formulation auxiliaries are the compounds mentioned above. The solvents and formulation auxiliaries are employed in the amounts customary for these substances.

The examples below are meant to illustrate the subject matter of the invention, but the subject matter of the invention is not meant to be limited to the examples.

EXAMPLE 1

Soft drinks were contaminated with the respective stated microorganisms. The active compound concentration required for disinfecting the beverages was determined by sterilization tests.
Nutrient Media: Yeast orange serum agar (from Oxoid CM657)
Substances: The substances used were employed neat or as ethanolic or butanolic solutions (for example 2.0% by volume) or suspensions. Dimethyl dicarbonate, Na benzoate, K sorbate, sorbic anhydride and benzoic anhydride were synthesized by known methods or were commercially available. The respective solutions were in each case freshly prepared (alcoholysis).
Apparatus: 50 ml tissue culture flasks from Greiner, gauze compresses from Holthans, Thoma counting chamber from Brand.

As a matter of principle, sterile reagents and apparatus were used. In addition to sterile disposable articles, the required apparatus and reagents were sterilized by suitable measures before use. Sterilization measures were heat treatment in a drying cabinet (at least 8 hours at about 120° C.) or in an autoclave (at least 15 minutes at about 120° C.).
Practice:
Filling of the Beverages:
Before the test was carried out, the beverage substrates were filled into tissue culture flasks. In general, the amount of beverage was 40 ml. Filling was carried out under sterile conditions. At this point in time, it was also possible for the persistent preservatives to be introduced.
Preparation of the Germ Suspension:
The cultures, which were grown under optimum conditions (in tissue culture flasks from Greiner; 50 ml, 25 cm$^2$ or in oblique agar tubes), were wetted with up to 30 ml (depending on the test germ) of NaCl solution (if appropriate with addition of about 3 drops of Tween 80), rinsed off or, using glass beads (depending on the germ), scrubbed off intensively and, if required, filtered. Alternatively, it was also possible to employ fluid cultures. Using a microscope and a Thoma chamber, it was possible to carry out a preliminary determination of the germ number. An accurate determination of the germ number of the germ solution used was carried out using the Koch inoculation plate method.
Addition of the Germ Suspension:
Depending on the given germ seed (for example 50-500 germs/ml of substrate), the appropriate volume of germ solution (original or dilution) were added and the sample was shaken intensively.
Addition of the Active Compounds:
The doses of active compound, added as pure substance or as appropriate alcoholic solution or suspension in the case of dimethyl dicarbonate and the carboxylic anhydrides, were then added. For a period of about 20 seconds, the samples were immediately shaken intensively.
Storage
The beverage samples were stored at a cultivation temperature of 26° C.±2° C.

Evaluation
In the case of formerly clear beverages, clouding indicates contamination. In the case of cloudy fruit pulp-containing beverages, visual evaluation was not always possible. Accordingly, in these cases evaluation was carried out as a germ number determination in agar.

The present invention is described with reference to specific details of particular embodiments thereof. It is not intended that such details be regarded as limitations upon the scope of the invention except insofar as and to the extent that they are included in the accompanying claims.

As used in this specification and the appended claims, the singular forms "a," "an," and "the" include plural referents unless the content clearly dictates otherwise.

TABLE 1

Activity of benzoic anhydride in apple juice against *Saccharomyces cerevisiae*

| Substances: | Benzoic anhydride 100, 150, 250 mg/l |
| | Dimethyl dicarbonate 250 mg/l |
| | Sodium benzoate 177 mg/l |
| Test germ: | *Saccharomyces cerevisiae* |
| Substrate: | Apple juice |
| pH: | 3.5 and 6.0 |

Effect of the test substances on the activity after the contact time of 24 hours at 20° C.
Germ seed per ml of substrate: 56 000 cfu/ml

| | | | Germ number after 24 h (carried out in duplicate) | | Visual evaluation after 4 weeks |
|---|---|---|---|---|---|
| Control (no active compound) | | pH 3.5 | >3 × 10$^6$ | 2.7 × 10$^6$ | + |
| | | pH 6.0 | 2.1 × 10$^6$ | 2.5 × 10$^6$ | + |
| Dimethyl dicarbonate | 250 | pH 3.5 | <10 | 160 | + |
| Not according to the invention | mg/l | pH 6.0 | 2060 | 830 | + |
| Benzoic anhydride | 100 | pH 3.5 | <10 | <10 | − |
| | mg/l | pH 6.0 | 100 | 45 | + |
| Benzoic anhydride | 150 | pH 3.5 | <10 | <10 | − |
| | mg/l | pH 6.0 | about 10 | about 10 | + |
| Benzoic anhydride | 250 | pH 3.5 | <10 | <10 | − |
| | mg/l | pH 6.0 | <10 | <10 | − |
| Na benzoate | 177 | pH 3.5 | 6.8 × 10$^5$ | 5.3 × 10$^5$ | + |
| Not according to the invention | mg/l | pH 6.0 | 2.6 × 10$^6$ | 2.2 × 10$^6$ | + |

− = not fermented
+ = fermented

EXAMPLE 2

The tests were carried out as stated in Example 1.

TABLE 2

Activity of sorbic anhydride in apple juice against *Saccharomyces cerevisiae*

| | | Germ number after 24 h (carried out in duplicate) | | Visual evaluation after 4 weeks |
|---|---|---|---|---|
| Control (no active compound) | | 1.8 × 10$^6$ | 1.1 × 10$^6$ | + |
| Dimethyl dicarbonate | 250 mg/l | <10 | <10 | + |
| Not according to the invention | | | | |
| Sorbic anhydride | 50 mg/l | <10 | <10 | − |
| Sorbic anhydride | 100 mg/l | <10 | <10 | − |
| Sorbic anhydride | 250 mg/l | <10 | <10 | − |
| Na benzoate | 177 mg/l | 1.3 × 10$^5$ | 1.1 × 10$^5$ | + |

TABLE 2-continued

Activity of sorbic anhydride in apple juice against *Saccharomyces cerevisiae*

| | Germ number after 24 h (carried out in duplicate) | | Visual evaluation after 4 weeks |
|---|---|---|---|

Not according to the invention

Substances:
Sorbic anhydride 50, 100, 250 mg/l
Dimethyl dicarbonate 250 mg/l
Sodium benzoate 177 mg/l
Test germ: *Saccharomyces cerevisiae*
Substrate: Apple juice
Effect of the test substances on the activity after the contact time of 24 hours at 20° C.
Germ seed per ml of substrate: 56.000 cfu/ml

EXAMPLE 3

The tests were carried out as Stated in Example 1.

TABLE 3

Activity of sorbic anhydride in apple juice against yeast mix

| | Germ number after 24 h (carried out in duplicate) | | Visual evaluation after 4 weeks |
|---|---|---|---|
| Control (no active compound) | $6.6 \times 10^6$ | $8.1 \times 10^6$ | + |
| Dimethyl dicarbonate 250 mg/l | $6.8 \times 10^6$ | $5.7 \times 10^6$ | + |
| Not according to the invention | | | |
| Sorbic anhydride 50 mg/l | $2.6 \times 10^5$ | $1.8 \times 10^5$ | + |
| Sorbic anhydride 100 mg/l | $9.2 \times 10^4$ | $9.4 \times 10^4$ | + |

TABLE 3-continued

Activity of sorbic anhydride in apple juice against yeast mix

| | Germ number after 24 h (carried out in duplicate) | | Visual evaluation after 4 weeks |
|---|---|---|---|
| Sorbic anhydride 250 mg/l | 985 | 1080 | − |
| Na benzoate 177 mg/l | $1.3 \times 10^5$ | $1.1 \times 10^5$ | + |
| Not according to the invention | | | |

Substances:
Sorbic anhydride 50, 100, 250 mg/l
Dimethyl dicarbonate 250 mg/l
Sodium benzoate 177 mg/l
Test germ: Mixture of different problem yeasts from a beverage filling unit.
Substrate: Apple juice
Effect of the test substances on the activity after the contact time of 24 hours at 20° C.
Germ seed per ml of substrate: 56.000 cfu/ml

What is claimed is:

1. A process comprising:
adding to a beverage a carboxylic acid anhydride corresponding to formula (I)

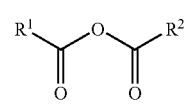
(I)

wherein
$R^1$ and $R^2$ are pent-1,3-dienyl,
further wherein the carboxylic acid anhydride corresponding to formula (I) is added to the beverage in an amount of from 50 to 250 ppm based on the beverage.

* * * * *